(12) United States Patent
Sanders

(10) Patent No.: US 6,660,470 B1
(45) Date of Patent: *Dec. 9, 2003

(54) METHODS OF IDENTIFYING BACTERIA OF SPECIFIC BACTERIAL GENUS, SPECIES OR SEROTYPE

(75) Inventor: Michael F Sanders, Basingstoke (GB)

(73) Assignee: The Central Science Laboratory (CSL) representing the Secretary of State of Environment, Food and Rural Affairs, Sad Hutton (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/225,448

(22) Filed: Jan. 6, 1999

Related U.S. Application Data

(62) Division of application No. 08/679,320, filed on Jul. 12, 1996, now Pat. No. 5,888,725, which is a continuation of application No. 08/403,898, filed on Mar. 28, 1995, now abandoned.

(30) Foreign Application Priority Data

Sep. 22, 1992 (GB) .............................................. 9220027
Sep. 22, 1993 (GB) .............................................. 9301989

(51) Int. Cl.[7] .................................................. C12Q 1/70
(52) U.S. Cl. ......................................................... 435/5
(58) Field of Search ............................... 435/5–8, 325, 435/34, 39, 948; 536/23.1; 935/58

(56) References Cited

U.S. PATENT DOCUMENTS

| | | | |
|---|---|---|---|
| 4,104,126 A | 8/1978 | Young | 195/103.5 A |
| 4,218,534 A | 8/1980 | LaBelle et al. | 435/5 |
| 4,861,709 A | 8/1989 | Ulitzur et al. | 435/6 |
| 5,085,982 A | 2/1992 | Keith | 435/5 |
| 5,888,725 A * | 3/1999 | Sanders | 435/5 |

OTHER PUBLICATIONS

Sigma Biochemicals, Organic Compounds Catalogue, "Adenosine 5'–Triphosphate (ATP) Bioluminescent Assay Kit" p. 51, 1992.

Hirsh, D. Rapid Detection of Salmonella in Certified Raw Milk by Using Charge Modified Filters and Felix–01 Bacteriophage, J. of Food Protection, 47(5):388–390, Mar. 1984.

* cited by examiner

Primary Examiner—Ralph Gitomer
(74) Attorney, Agent, or Firm—Nixon & Vanderhye P.C.

(57) ABSTRACT

A method for detection, identification and/or quanification of target organisms of specific bacterial genus, species or serotype, based upon the occurrence of release of cell contents, particularly nucleotides, e.g., ATP, on lysis of bacterial cell walls on incubation with bacteriophages (phages) specific for them. When new phase particles are released at the end of the phage replication cycle nucleotide levels are measured and compared with controls. The method provides for the detection of specific bacteria which does not require insertion of the lux gene into the phage genome yet is faster and more sensitive than known non-modified phage utilizing techniques. The method is only limited by the availability of phage types suitable for selective attack of the target bacterial to be detected and can detect a single Salmonella in a sample of milk in under 12 hours.

17 Claims, No Drawings

METHODS OF IDENTIFYING BACTERIA OF SPECIFIC BACTERIAL GENUS, SPECIES OR SEROTYPE

This is a division of application Ser. No. 08/679,320, filed Jul. 12, 1996, now U.S. Pat. No. 5,888,725 which is a continuation of Ser. No. 08/403,898 filed Mar. 28, 1995, now abandoned.

The present invention relates to a method of detection, identification and/or quantification of bacteria and to test kits for carrying it out. Particularly the method enables detection of organisms of specific bacterial genus, species or serotype, in isolated form or as contaminants in environmental or forensic samples, or in foodstuffs.

There are many requirements for methods of screening for specific bacteria, particularly those present in low numbers and in specific environments; for example, human bacterial pathogens in contaminated foods. Public health and quality control bodies demand rapid bacterial detection methods which have suitable levels of specificity and sensitivity, but few satisfactory methods exist.

It is known to detect specific bacteria by use of genetically engineered bioluminescent bacteriophages, virus particles which have had the 'lux' gene inserted into their genome, as described by Ulitzer and Kuhn, in Scholuerich et al (Eds.) 'Bioluminescence and Chemiluminescence-new perspectives' pages 463–472; pub. (1987) by John Wiley and Sons. The 'lux' gene is that encoding for bacterial luciferase and the technique is based upon the fact that upon infection of a target bacterium, bacteriophage genes and the lux gene are injected into it and are subsequently expressed. The presence of the target bacterium is indicated by emission of light from the sample which can easily be measured. Most bacteria are susceptible to attack by bacteriophages (commonly called phages), many of which lyse or disrupt their host at the end of their replication process, and these interactions show varying degrees of host/phage specificity.

Schutzbank et al, The Use of "Bioluminescent Bacteriophages" for the Detection and Identification of Salmonella in Foods, Rapid Methods and Automation in Microfiology and Immunology, 1987, 5$^{th}$ ed., p 241–251, Berscia, Brixia Academic Press, 1987 have shown the potential or this technique but note problems with cross reactivity between construct phages and other non-target bacterial types. While such problems may be overcome by engineering more specific phages, see for example U.S. Pat. No. 4,348,478. this entails provision of phages for each type of target bacteria for which a need to test exists. Such recombinants may not readily be constructed for a variety of reasons, not least of which being the need to avoid disruption of the function of the phage itself.

Initially only Salmonella and E. coli phages were successfully modified. This is because a great deal of work had been previously done on the molecular biology of these organisms and it was known that the lux genes could fit into the phage head without causing lose of the phage's ability to be infective. This is not the case with other food pathogens and a massive amount of work will need to be done before a comprehensive range of modified phages can be constructed.

A further method utilising the specificity of phages for their host bacteria is disclosed by Hirsh and Martin (1984) Journal of Food Protection, Vol 47, No 5, pp388–390. This method relies on the phage induced destruction of the bacteria grown on enrichment broth to produce lacunae in the bacterial lawns, wherein lacunae are indicative of the presence of the target bacterium; in this case a Salmonella. However the method is lengthy to perform, requiring about 24 hours for a positive result, and in only sensitive to 5 cells/ml or more.

The present inventor has now provided a method based upon the occurrence of release of cell contents on damage, e.g. lysis, of cell walls of bacteria when new phage particles are released at the end of the phage replication cycle. This method provides for the detection of specific bacteria which does not require insertion of the lux gene into the phage genome, whereby specificity is only limited by the availability of phage types suitable for selective attack of the target bacteria to be detected, yet its performance takes far less time than the existing unmodified phage techniques. Thus the method of the present invention has more readily realised potential for the specific and rapid detection of almost any bacteria in any environment; (foodstuffs, drinking water, pharmaceutical products and diseased tissues in humans, animals and plants etc.) provided that a phage with the necessary specificity can be found. Use of the method of the present invention has been shown to be capable of detection or a single Salmonella in a 1 ml sample of milk in under 12 hours.

Thus the present invention provides a method for the detection, identification and/or quantification of target organisms of specific bacterial genus, species or serotype present in a material comprising incubating the material or bacteria derived therefrom with bacteriophage selected for the ability to specifically infect target organisms and release cellular components from them, measuring the amount of one or more particular components released from any bacteria present during the incubation, and relating this to the presence, identity and/or amount of target organisms. Preferably incubation of material with bacteriophage is carried out in bacterial support medium.

Preferred cellular component comprises nucleotides. Theoretically it is possible to measure any or the nucleotides that are released by the cell lysis caused by the release of new phage particles, for example NAD, NADP, NADH, NADPH, ATP or ADP, cAMP or cGMP, with sensitivity provided by use of one or more of the many enzyme based assay systems, e.g. 'cascade' systems, that are available in the art. For example, GB 2213261 discloses a method which may be used for assaying reduced pyridine nucleotides, e.g. NADH or NADPH, based upon a salicylate monooxygenase system, while other enzyme systems such as the alkaline phosphatase/NAD/NADP system as disclosed in GB 2240845. Suitable assays for ADP, cAMP, cGMP etc will occur to those skilled in the art.

However, particularly preferred is the measurement of adenosine triphosphate (ATP), that being readily measurable by assay with a variety of enzyme/enzyme substrate combinations by virtue of its being a cofactor in numerous substrate conversions, and being released in relatively large quantities as compared with other bacterial nucleotides. For the rapid and efficient determination of levels of released ATP it is especially preferred to utilise enzyme reactions which result in production or luminescence, most conveniently using luciferase. ATP release is quantifiable with commercially available reagents using bioluminescence wherein it is used to drive oxidation of luciferin under catalysis by luciferase resulting in the emission of light. The quantum efficiency of this reaction is extremely high and the presence and amount of light produced gives a measure of ATP released and thus of the presence and numbers of target organisms.

For identification or quantification of specific bacteria occuring in material in relatively high concentrations, e.g. in cultures of isolated bacteria, it is possible merely to incubate the specific phage with a part of that culture or a subculture in the presence of, or with subsequent addition of, the component assay reagents and thus to measure the amount of component released by performing the assay.

For identification, detection and/or quantification of specific bacteria at lower concentrations, for example as contaminants in or on water or foodstuff materials, it is necessary to first perform an enrichment or bacteria derived from the material under test, e.g. for a few hours, to allow the target bacterium to multiply to a level where its released components, e.g. nucleotides, will be detectable above background levels. Enrichment is preferably carried out by culturing a selective medium, favouring growth of target bacteria, that has been inoculated with the material or a culture derived therefrom, e.g. derived from a swab. Typically enrichment lasts less than a working day, e.g. 1 to 10 hours; preferably 1 to 5 hours.

After enrichment, one or more phage types with known target host specificities are mixed with the culture and the mixture is incubated. During the incubation period infection or specific target bacteria with phage occurs and the replication cycle begins. At the end of the replication cycle target bacteria present burst (times range from e.g. 20–60 minutes depending on species), cellular component, e.g. nucleotide, is released and detected. Control samples either containing no bacteria, non-target bacteria or bacteria without phage show no substantial increase in levels above background levels.

Furthermore, dependent upon the biology of the phage/host pair selected, the method has the potential for great specificity and still further sensitivity and rapidity. Utilising the aforesaid ATP assay method the inventor has readily developed systems for the detection of several human pathogens in milk including *Staphlococcus aureus, Listeria monocytogenes* and Salmonella, and others for foodstuffs such as lettuce whereon pathogens such as Listeria are known to be a potential danger. Salmonella, Listeria, Staphylococci, *E. coli* and pseudomonads have all proved to be readily detectable by the method. It will be seen by those skilled in the art however that there is no limit to the application of the present method other that the availability of the necessary specific phage or phages.

In a more preferred embodiment of the present invention it has been found to be advantageous to incubate a sample of material under investigation with a nonselective bacterial support medium, e.g. such as peptone water or Brain Heart Infusion broth (B.H.I), in order to activate or 'resuscitate' substantially all or the bacteria present therein, before carrying out any enrichment incubation. Such incubation is conveniently, but not essentially, carried out for 1–5 hours; but as with the enrichment, shorter or longer periods may be appropriate depending on, inter alia, the freshness or the material.

In a preferred embodiment a sample of the resuscitated material is then transferred to a selective medium adapted to favour growth of the bacteria being investigated over interfering bacteria and incubated for a further period, e.g. 1–5 hours. Conveniently an aliquot of the medium from the resuscitation stage is so transferred.

After the incubations are complete all or part of the cultured media is mixed with the selected phage, e.g. phage in the form of a suspension or freeze dried, and incubated for a set time and at a set temperature selected according to the biological characteristics of the phage/bacteria combination being used. The amount of component, e.g. nucleotide, whose release is being measured is then measured using an appropriate assay, e.g. enzyme/substrate system.

For assaying the release of cellular component completed resuscitation or selective enrichment step medium, or a medium with a sample of the material itself, is conveniently mixed with the selected phage in a vessel, e.g. for ATP In a luminometer tube, and incubated for a suitable time and suitable temperature. e.g. 30 to 60 minutes at 20° C. to 40° C. to allow call lysis; these conditions depending on the phage/bacteria system. For measuring ATP, light producing assay reagents, e.g. those of the luciferin/luciferase system, can be added before or after this incubation period or the lysis period; light produced over the period or on addition is detected in a luminometer and related to the amount of ATP released. In all cases controls are advantageously carried out for comparison of background component levels, e.g. nucleotide levels, in samples incubated without the phage or incubated with phage and a known amount of target bacteria whereby production of calibration curves for assessing bacteria numbers is enabled. Such controls may include challenge with other phages of different specificity in order to more completely determine the characteristics of the organisms present in the material. Similarly several phage types may be used in the same incubation where the method is being used to screen for a number or types of bacteria for which no one common phage is specific.

The range of bacteriophages available and the bacteria for which they are specific will be realised to be vast by those skilled in the art. For example a list of phage types available from the American Type Culture Collection (ATCC) is published by them as 'Catalogue of Bacteria & Bacteriophages'. Other such depositories also publish equivalent data in their catalogues and this may be used to identify possible phage 'reagents' for the present method. Phages may be used, inter alia, in aqueous suspension or in freezed dried form e.g. on microtitre plate wells. In this manner plate luminometry can be used. Preferred phages are lytic and lead to lysis of the target organism.

In addition to deposited phages, a further source or phages is provided by isolating them from suitable environments; that is conveniently the environment where the target bacteria are themselves to be found. For example, it is possible to isolate phages specific to both Campylobacter spp. and Salmonella spp. from effluent from a poultry processing plant. Isolation techniques will be well known to those skilled in the art but are exemplified by Loessner and Busse (1990) Applied and Environmental Microbiology Vol 56, pp1912–1918, and Adams 'Bacteriophages' Pub Interaciance Inc (1959) pp447–455.

The range of media available for selective promotion or growth of a particular bacterial type will also be known to those skilled in the art and thee way function by positive action or by e.g. inhibition of other organisms. Examples of such media are illustrated by reference to supplier's manuals, e.g. such as those available from UNIPATH Limited, Wade Road, basingstoke, HANTS, RG24 OPW, UK 'Selective Microbiology for Food and Dairy Laboratories', or e.g. the OXOID manual. These publications list, for example, media capable of favouring growth of Campylobacter, Listeria and Yersinia. Similarly methods for isolation or food pathogens for preparation or test samples are well known. (UNIPATH and OXOID are Registered Trade Marks).

The present invention also provides test kits for carrying out the method or the present invention and these are characterized in so far as they comprise a bacteriophage selected for the ability to specifically infect bacterial target organisms, ie. a type or types for which detection, identification and/or quantification is desired, in combination with some or all or the reagents which are specifically associated with the aforesaid method of the invention.

Thus preferably test kits of the present invention comprise; (a) a bacteriophage selected for its ability to specifically infect target bacterial organisms and release cellular components from them, preferably in a form substantially free of such target organisms, and (b) the reagents necessary for carrying out assay of the amount of one or more cellular components released by the action of the bacteriophage on the bacterial organism.

Optionally the kits further comprise (c) a selective medium for promoting preferential growth of target bacterial organisms and/or (d) a non-selective bacterial growth medium.

Thus preferred test kits of the invention are those wherein the reagents necessary for carrying out assay are for assay of the amount or a nucleotide present in a sample, preferably comprising luciferin and luciferase. Test kits optimised for performance of high sensitivity assay of bacteria will include both non-selective and selective growth media, the non-selective growth medium being preferably that suitable for a microorganism resuscitation step.

It will be realised that, unlike the prior art method which monitors lacunae on solid media supported bacterial lawns, the present method is particularly adapted to test for bacteria derived from samples of material under investigation by culturing on liquid media, although solid media may of course be used. A particular kit for performance of the present method may be one having the bacteriophage component (a) together with one or more media (c) and/or (d) of liquid form or concentrated or dry components adapted for the preparation of such liquid medium. While many such combinations adapted for the performance of the method of the present invention will occur to those skilled in the art, the most complete form of the kit will comprise all the reagents (a) to (d); the nucleotide assay components preferably being optimised for measuring nucleotide levels in a sample of the bacterial growth medium. Where quantification is desired samples or the bacteria might also be included, e.g. as spores or in cells in a medium, for setting up control readings of known levels of bacteria for calibrating the nucleotide assay. Target and control non-target organisms may be used.

The method and kits of the present invention will now be exemplified by way of illustration only by reference to the following non-limiting examples. The vast variety of options available will be readily determinable by those skilled in the art on consideration of the general method described above and particularised below, and the available types of bacteriophages and nucleotide assays.

EXAMPLE 1

Protocol And Test Kit for Detection of Low Levels of Salmonella in Milk by Phage-mediated ATP Bioluminescence Strains Used the strain of bacterium to be detected was a Salmonella which had been isolated from poultry processing plant effluent water. Prior to investigations stock cultures of bacteria were maintained on Brain Heart Infusion (B.H.I.) agar (Unipath Ltd., Basingstoke, Hampshire) slants. The specific bacteriophage, Sal1, was also isolated from this source.

The bacteriophages were stored as bacteria-free lysates in 1.5 ml cryotubes above liquid nitrogen; the titre of bacteriophage lysate used was $1.2 \times 10^9$ plaque-forming units (p.f.u.) per milliliter.

Brain Heart Infusion broth (BHI)-Unipath Ltd. was used to grow the inoculum. Serial dilutions of broth culture were made using 0.1M potassium phosphate buffer (pH 7). Selective enrichment was shown to be achieved using Rappaport-Vassiliadis (R.V.) broth (Unipath Ltd.), and more preferably Selenite Cystine (S.C) broth (Difco Laboratories, Detroit, Mich.).

A suitable kit for detection of this Salmonella using the method or the present invention was provided comprising (a) specific bacteriophage Sal1, (b) luciferin/luciferase assay reagents (e.g. as below) and/or (c) R.V. or S.C. broth and optionally included (d) B.H.I. Sal1 is optionally provided as infected bacteria which are completely lysed to liberate phage and destroy bacteria before use.

The spectrophotometer used was model CE 202 (Cecil Instruments, Cambridge, England) with 1 cm disposable cuvettes (Whatman International Ltd., Maidstone, England). Light measurements were made using a luminometer, model LB953 Autolumat (Berthold Instruments U.K. Ltd., St. Albans, Hertfordshire), and disposable polystyrene tubes (catalogue number 55.476; Sarstedt, Beaumont Leys, Leicester, U.K.). The adenosine 5'-triphosphate assay reagents were luciferin/luciferase and adenosine 5'-triphosphate assay mix dilution buffer and were obtained from Sigma Chemical Co Limited, Poole, Dorset. Luciferin/luciferase reagent was diluted 1:25 with the buffer when required.

Preparation of Inoculum

A broth culture of Sal1 was set up in 10 ml B.H.I. broth and incubated at 37° C. until visibly turbid. Absorbance at 650 nm was measured, and simultaneously a tenfold dilution series from $10^0$ through to $10^{-10}$ was prepared in potassium phosphate buffer. From each dilution of culture five 1 ml samples were inoculated with fresh 9 ml volumes of B.H.I. broth. These tubes were then incubated overnight at 37° C. and observed for turbidity. From published tables ("Theory and Practice in Experimental Bacteriology". G. G. Neynell & Elinor Meynell, Cambridge University Press) it was possible to determine which culture dilution contained approximately 100 cells per milliliter and that dilution was used to prepare samples for testing.

i) Protocol: Milk Test: Sampling and Enrichment Procedure

A 1 ml sample of 100 ml fresh pasteurised milk infected with approximately 1 cell per milliliter of log-phase Sal1 at room temperature was transferred into 9 ml fresh B.H.I. broth and incubated for 2 hours at 37° C. as a resuscitation/enrichment step. Either (a)0.1 ml or this medium was then placed in 10 ml Rappaport-Vassiliadis (RV) selective-enrichment broth and incubated at 41° C. for 7 hours.

Alternatively, where it was suspected that the viability of bacteria in the sample is poor, a less potent selective medium was applied, as death of weakened bacterial cells was recorded in presence of R.V. medium in some cases. The 'milder' medium was selected was Selinite Cystine broth wherein (b) 1.0 ml of the completed resuscitation/enrichment step medium was placed in 9 ml Selenite Cystine selective enrichment broth and incubated at 35° C. overnight, with the 1 ml or the resultant culture used to inoculate 9 ml fresh B.H.I. which was then incubated at 37° C. for 2 hours as a recovery step.

In either case (a) or (b), 4.5 ml of the completed culture was mixed with 0.5 ml specific bacteriophage suspension Sal1. The remainder of the R.V., Selinite Cystine or B.H.I recovery culture was retained.

(ii) Preparation of Luminometer and Light Measurement 50 microliters B.H.I., held at 37° C., was added to all 80 polystyrene luminometer tubes in the luminoneter, which itself had been pre-warmed to 37° C. 50 microliters of the R.V. or B.H.I cultures, dependent upon the protocol selected, to which bacteriophages had been added was placed in each alternate tube in the luminometer, and 50 microliters of the respective culture without bacteriophages was added to the remaining tubes as the negative control. Light measurement was then commenced. with 100 microliters of luciferin/luciferase reagent injected into each tube and light output immediately monitored over periods or 60 seconds. Measurements were then plotted as peak light intensity against time for both positive and negative control tubes.

Using either protocol a peak or 25 000 counts per second (c.p.s.) was obtained after 60 minutes for positive tubes, with the negative controls reaching only 500 c.p.s.

EXAMPLE 2

Protocol and Test Kit for the Detection of Listeria Monocytogenes in Lettuce by Phage Mediated ATP Bioluminescence Strain Used The strain of *Listeria monocytogenes* used was ATCC 23074 with its specific bacteriophage ATCC 23074-B1. The bacteriophage was stored as a bacteria-free lysate in 1.5 ml cryotubes above liquid nitrogen. The titre of the phage preparation was approximately $2.11 \times 10^{10}$ p.f.u. per milliliter.

Culture Media

Stock cultures were maintained on Brain Heart Infusion (B.H.I.) agar slants. B.H.I. broth was used for growth of inocula. Serial dilutions were made using potassium phosphate buffer (0.1 M. pH7). The selective-enrichment medium was Listeria Enrichment Broth (L.E.B.). All culture media were obtained from Unipath Ltd., Basingstoke, Hampshire, U.K.

A suitable kit for the determination of *Listeria monocytogenes* by the method of the present invention was provided comprising (a) bacteriophage ATCC 23074-B1. (b) the luciferin/luciferase assay reagents and/or (c) L.E.B and optionally included B.H.I.

Apparatus: The spectrophotometer, cuvettes, luminometer and polystyrene luminometer tubes were as detailed in the salmonella protocol. A Colworth 400 stomacher was used (A. J. Seward, London SE1).

Reagents: Luminescence reagents were as described in the Salmonella protocol.

Preparation of Inoculum

An inoculum of ATCC 23074 containing approximately 100 cells per milliliter was prepared in the same way as described in the Salmonella protocol.

Inoculation of Lettuce for Use as Positive Test

Fresh lettuce was chopped by hand into pieces approximately 2 centimeters in length. 100 mls of the buffer suspension of Listeria prepared in step (i) was added to 100 grams or chopped lettuce and mixed well by shaking for 1 minute. The lettuce was then drained and stored at 4° C.

i) Extraction and Enrichment Procedures for Listeria

The inoculated lettuce was placed in a large stomacher bag with 100 mls potassium phosphate buffer and mixed in the stomacher for 1 minute. 1 ml of the resultant suspension was then added to 9 ml B.H.I. broth and incubated at 30° C. for 4 hours as a resuscitation/enrichment step. 1 ml of this culture was then added to 9 ml L.E.B. at 30° C. and incubated overnight, this being the selective-enrichment step. 4.5 ml of this culture was then removed and 0.5 ml or specific bacteriophage ATCC 23074-B1 was added to that.

The remaining L.E.B. culture was kept as the negative control.

ii) Preparation of Luminometer and Light Measurement 50 microliters warm (30° C.) B.H.I. was added to 80 tubes in the luminometer, which had been pre-warmed to 30° C. The machine was set to run in kinetics mode at 30° C. To the first tube, and to each alternate tube after it, was added 50 microliters or the negative control culture (without bacteriophages). To the remaining tubes was added 50 microliters of the test culture (with bacteriophages). 100 microliters luciferin/luciferase reagent was then injected into each tube in turn and the light output immediately measured over periods of 60 seconds.

As with Salmonella the peak light intensity (counts per second) for the test and negative control tubes was plotted against time. Following this protocol, a peak or 10 000 c.p.s. was observed for the test culture after 48 minutes whilst the negative control remained constant with approximately 1000 c.p.s. The absence or light output levels above the control is interpreted as absence or target Listeria organisms and not absence of bacteria per se.

EXAMPLES 3 to 11

Further examples of bacteria and particular phage that are capable of specifically releasing their cell contents, including ATP, are listed below with media and preferred incubation temperature suitable for incubating these together for the purpose or the present method.

| EXAMPLE No | BACTERIA | PHAGE | MEDIUM | TEMP |
|---|---|---|---|---|
| 3 | *Lactococcus lactis* sp *cremoris* ATCC11603 | ATCC 11603-B1 | M17 Broth Unipath | 26° C. |
| 4 | *Enterococcus faecium* ATCC19950 | ATCC 19950-B1 | M17 Broth Unipath | 37° C. |
| 5 | *Staphylococcus aureus* subsp. *aureus* ATCC 11988 | ATCC 11988-B1 | BHI (Oxoid) CM 225 Unipath | 37° C. |
| 6 | *Bacillus cereus* ATCC 12826 | ATCC 12826-B1 | BHI (Oxoid) CM 225 Unipath | 30° C. |
| 7 | " ATCC 27877 | ATCC 27877-B1 | BHI (Oxoid) CM 225 Unipath | 30° C. |
| 8 | *Enterobacter cloecae* ATCC 23355 | ATCC 23355-B1 | BHI (Oxoid) CM 225 Unipath | 30° C. |
| 9 | *Staphylococcus aureus* subsp. *aureus* ATCC 11987 | ATCC 11987-B1 | BHI (Oxoid) CM 225 Unipath | 37° C. |
| 10 | *Shigella dysenteriae* (Shiga) Castellani & Chalmers ATCC 11456a | ATCC 11456a-B1 | BHI (Oxoid) CM 225 Unipath | 37° C. |
| 11 | *Shigella dysenteriae* ATCC 23351 | ATCC 23351-B1 | BHI (Oxoid) CM 225 Unipath | 37° C. |

What is claimed is:

1. A method for identifying a target bacteria of a specific bacterial genus, species or serotype present in a sample comprising the steps of:
   (1) incubating the sample with a bacteriophage which has not been modified to include a lux gene and is selected for the bacteriophage's ability to specifically infect the target bacteria,
   (2) lysing the target bacteria releasing the bacteria's cellular components
   (3) detecting the cellular components released when the target bacteria is lysed, and (4) correlating the cellular components detected in step (3) with the presence of the target bacteria in the sample.

2. The method as claimed in claim 1 wherein incubating step (1) is carried out in a bacterial support medium.

3. The method as claimed in claim 1 wherein the sample is incubated in step (1) at a temperature of 20° C. to 40° C.

4. The method as claimed in claim 1 wherein the cellular components released in step (2) are detected in step (3) with an enzyme.

5. The method as claimed in claim 4 wherein the cellular component is ATP which is detected with an enzyme resulting in the production of luminescence.

6. The method as claimed in claim 5 wherein the enzyme is a luciferin/luciferase system and luminescence is measured.

7. The method as claimed in claim 1 wherein the sample is incubated with the bacteriophage in step (1) in the presence of or with subsequent addition of an assay reagent for identifying the cellular components released.

8. The method as claimed in claim 1 wherein the sample is incubated in step (1) with a selective medium for growing the target bacteria for a period of from 1 to 10 hours prior to incubating with the bacteriophage.

9. The method as claimed in claim 1 wherein the sample is incubated in step (1) with a non-selective medium supporting bacterial growth for a period of from 1 to 5 hours prior to the incubating with the bacteriophage.

10. The method as claimed in claim 1 wherein the sample is incubated in step (1) with the bacteriophage for a period of from 20 to 60 minutes.

11. The method as claimed in claim 1 wherein the sample is incubated in step (1) with a non-selective medium supporting bacterial growth and a portion of the incubated non-selective medium is then incubated with the bacteriophage.

12. The method as claimed in claim 1 wherein the sample is incubated in step (1) with a non-selective medium supporting bacterial growth and a portion of the incubated non-selective medium is then incubated with a selective medium for growing the target bacteria and thereafter is incubated with the bacteriophage.

13. The method as claimed in claim 1 wherein the bacteriophage is provided as a suspension, as freeze dried phage or as infected bacteria which are lysed prior to incubating.

14. The method as claimed in claim 1 wherein a plurality of bacteriophages are used in incubation step (1) and the presence of one or more types of target bacteria are identified.

15. A method according to claim 1, wherein nucleotide detected in step (3) is quantified and is correlated in step (4) to quantify the target bacteria.

16. A method for quantifying a target bacteria of a specific bacterial genus, species or serotype present in a sample comprising the steps of:

(1) incubating the sample with a bacteriophage which has not been modified to include a lux gene and is selected for the bacteriophage's ability to infect specifically the target bacteria and lyse that bacteria to release its cellular components, (2) detecting and quantifying the cellular components released when the target bacteria is incubated with the bacteriophage, and (3) correlating the cellular components detected and quantified in step (2) to quantify the target bacteria in the sample.

17. A method for identifying the presence of bacteria of a specific bacterial genus, species or serotype present in a sample comprising the steps of:

(1) incubating the sample with a bacteriophage which has not been modified to include a lux gene and is selected for the bacteriophage's ability to infect specifically a target bacteria and lyse that bacteria to release the bacteria's cellular components, (2) detecting the cellular components released when the target are lysed with the bacteriophage, and (3) correlating the cellular components detected in step (2) to identify the presence of the target bacteria in the sample.

* * * * *

UNITED STATES PATENT AND TRADEMARK OFFICE
CERTIFICATE OF CORRECTION

PATENT NO.     : 6,660,470 B1                                             Page 1 of 1
DATED          : December 9, 2003
INVENTOR(S)    : Sanders It is certified that error appears in the above-identified patent and that said Letters Patent is hereby corrected as shown below:

<u>Title page,</u>
Item [73], Assignee, should read as follows:

-- [73]  The Central Science Laboratory (CSL) representing The Secretary of State for Environment, Food and Rural Affairs, Sand Hutton (GB) --.

Signed and Sealed this

Sixteenth Day of March, 2004

JON W. DUDAS
*Acting Director of the United States Patent and Trademark Office*